(12) United States Patent
Mader et al.

(10) Patent No.: US 7,282,595 B2
(45) Date of Patent: Oct. 16, 2007

(54) ANTITUMOR BENZOYLSULFONAMIDES

(75) Inventors: Mary Margaret Mader, Fishers, IN (US); Luisa Maria Martin-Cabrejas, Madrid (ES); Michael Enrico Richett, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/535,002

(22) PCT Filed: Nov. 13, 2003

(86) PCT No.: PCT/US03/35041

§ 371 (c)(1),
(2), (4) Date: May 12, 2005

(87) PCT Pub. No.: WO2004/048329

PCT Pub. Date: Jun. 10, 2004

(65) Prior Publication Data

US 2006/0106053 A1    May 18, 2006

(51) Int. Cl.
*C07D 333/62* (2006.01)
(52) U.S. Cl. ...................................................... 549/55
(58) Field of Classification Search ................... 549/55
See application file for complete search history.

(56) References Cited

U.S. PATENT DOCUMENTS 5,405,727 A * 4/1995 Wilson et al. ........... 430/108.2

FOREIGN PATENT DOCUMENTS

| EP | 0 614 887 | 9/1994 |
|---|---|---|
| WO | WO 02 98848 | 12/2002 |

\* cited by examiner

*Primary Examiner*—Rebecca Anderson
*Assistant Examiner*—Shawquia Young
(74) *Attorney, Agent, or Firm*—Tina M. Tucker

(57) ABSTRACT

The present invention provides antitumor compounds of the formula (I); and antitumor methods.

5 Claims, No Drawings

ANTITUMOR BENZOYLSULFONAMIDES

In recent years fundamental advances have been made in the development of chemical agents and regimens of therapy to combat neoplastic diseases. Despite these continuing advances, cancers continue to exact intolerable levels of human pain and suffering. The need for new and better methods of treating malignant neoplasms and leukemias continues to fuel efforts to create new classes of compounds, especially in the area of inoperable or metastatic solid tumors. The recent avalanche of information regarding the basic biological processes involved in neoplasms has led to a deeper understanding of the heterogeneity of tumors. It is because of this extreme heterogeneity among populations of neoplastic cells that new chemotherapeutic agents should have a wide spectrum of activity and an acceptable therapeutic index. In addition, such agents must be chemically stable and compatible with other agents. It is also important that any chemotherapeutic regimen be as convenient and painless as possible to the patient.

Chemotherapy and radiation are frequently used in the treatment of cancer and, although they often produce some response in the malignant disease, they are rarely curative. Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al., *Cell*, 88, 277-285 (1997)). Because angiogenesis is a critical component of the mass expansion of most solid tumors, the development of new agents for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

The present invention provides novel N-[benzoyl]-bicyclylsulfonamide compounds useful in the treatment of susceptible neoplasms.

The present invention provides a compound of Formula I:

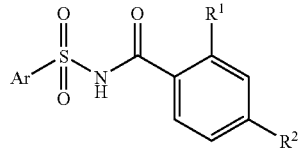

where:
Ar is

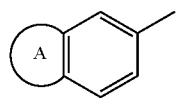

or a heterocycle selected from the group consisting of 2,3-dihydrobenzo[1,4]dioxin-6-yl, 2,3-dihydrobenzofur-5-yl, benzo[1,3]dioxol-5-yl, 1-($C_1$-$C_6$ alkyl)indolin-6-yl, benzothien-2-yl, benzothien-5-yl, 5-($C_1$-$C_6$ alkyl)benzothien-2-yl, 6-($C_1$-$C_6$ alkyl)benzothien-2-yl, benzothiazol-6-yl, benzofur-2-yl, benzofur-6-yl, thieno[3,2-b]pyridin-2-yl, and 1-($C_1$-$C_6$ alkyl)indol-2-yl;

A is phenyl, benzofuryl, cyclopentadienyl, cyclobutyl, or a cyclopentyl that is optionally substituted at one of the two carbons adjacent to the ring fusion of the cyclopentyl with an oxo moiety;

$R^1$ and $R^2$ are either both halo, both trifluoromethyl, or one is halo and the other is $C_1$-$C_6$ alkyl; or a pharmaceutically acceptable base addition salt thereof.

The present invention further provides a method of treating susceptible neoplasms in a mammal comprising administering to a mammal in need of such treatment an oncolytically effective amount of a compound of Formula I or a pharmaceutically acceptable base addition salt thereof.

The present invention also provides a method of suppressing tumor angiogenesis in a mammal comprising administering to a mammal in need of such treatment an angiogenesis suppressing amount of a compound of Formula I or a pharmaceutically acceptable base addition salt thereof.

The present invention also provides a pharmaceutical formulation comprising a compound of Formula I or a pharmaceutically acceptable base addition salt thereof in combination with a pharmaceutically acceptable excipient.

This invention also provides the use of a compound of Formula I for the manufacture of a medicament for the treatment of susceptible neoplasms. Additionally, this invention provides a pharmaceutical formulation adapted for the treatment of susceptible neoplasms containing a compound of Formula I. Furthermore, this invention includes a method for the treatment of susceptible neoplasms that comprises administering an effective amount of a compound of Formula I.

The general chemical terms used in the formulae above have their usual meanings. For example, the term "$C_1$-$C_6$ alkyl" includes methyl, ethyl, propyl, isopropyl, butyl, isobutyl, sec-butyl, tert-butyl, pentyl, and hexyl moieties. The term "halo" is taken to mean chloro, bromo, fluoro, and iodo.

The term "mammal" is taken to mean any of various warm-blooded vertebrate animals of the class Mammalia, most preferably humans, characterized by a covering of hair on the skin and, in the female, milk-producing mammary glands for nourishing the young.

While all of the compounds of Formula I are useful antitumor agents, certain classes of compounds are preferred. The following paragraphs describe such preferred classes.

a) Ar is 2,3-dihydrobenzo[1,4]dioxin-6-yl;
b) Ar is benzo[1,3]dioxol-5-yl;
c) Ar is 1-($C_1$-$C_6$ alkyl)indol-2-yl;
d) A is cyclopentadienyl;
e) A is cyclopentyl;
f) The compound is a pharmaceutically acceptable base addition salt;
g) The compound is a sodium salt.

It will be understood that the above classes may be combined to form additional preferred classes.

The compounds of Formula I are antineoplastic agents. Thus, the present invention also provides a method of treating a susceptible neoplasm in a mammal that comprises administering to a mammal in need of said treatment an oncolytically effective amount of a compound of Formula I. The present compounds are believed to be useful in treating susceptible neoplasms, including tumors and carcinomas, such as of the central nervous system: glioblastoma multiforme, astrocytoma, oligodendroglial tumors, ependymal and choroid plexus tumors, pineal tumors, neuronal tumors, medulloblastoma, schwannoma, meningioma, meningeal sarcoma; neoplasms of the eye: basal cell carcinoma, squamous cell carcinoma, melanoma, rhabdomyosarcoma, retinoblastoma; neoplasms of the endocrine glands: pituitary neoplasms, neoplasms of the thyroid, neoplasms of the adrenal cortex, neoplasms of the neuroendocrine system, neoplasms of the gastroenteropancreatic endocrine system; neoplasms of the gonads; neoplasms of the head and neck: head and neck cancer, oral cavity, pharynx, larynx, odontogenic tumors; neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, veriform appendix and peritoneum, adneocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, addenocarcinoma of the uterine corpus, ovarian cancer, gynecologic sarcomas; neoplasms of the breast; neoplasms of the skin: basal cell carcinoma, squamous cell carcinoma, dermatofibrosarcoma, Merkel cell tumor; malignant melanoma; neoplasms of the bone and soft tissue: osteogenic sarcoma, malignant fibrous histiocytoma, chondrosarcoma, Ewing's sarcoma, primitive neuroectodermal tumor, angiosarcoma; neoplasms of the hematopoietic system: myelodysplastic sydromes, acute myeloid leukemia, chronic myeloid leukemia, acute lymphocytic leukemia, HTLV-1 and T-cell leukemia/lymphoma, chronic lymphocytic leukemia, hairy cell leukemia, Hodgkin's disease, non-Hodgkin's lymphomas, mast cell leukemia; and neoplasms of children: acute lymphoblastic leukemia, acute myelocytic leukemias, neuroblastoma, bone tumors, rhabdomyosarcoma, lymphomas, renal tumors. In particular, the present compounds are believed to be useful in treating solid tumors, especially tumors of the colon and rectum. It is preferred that the mammal to be treated by the administration of the compounds of Formula I is human.

The compounds of the present invention are acidic in nature and accordingly may react with any of a number of inorganic and organic bases to form pharmaceutically acceptable base addition salts. It is preferable to convert the compounds of Formula I to their pharmaceutically acceptable base addition salts for ease of administration when aqueous solutions of the subject compound are required. The Formula I compounds can react with basic materials such as alkali metal- or alkaline earth metal hydroxides, carbonates, and bicarbonates including, without limitation, sodium hydroxide, sodium carbonate, potassium hydroxide, calcium hydroxide, and lithium hydroxide to form pharmaceutically acceptable salts such as the corresponding sodium, potassium, lithium, or calcium salt. The sodium and potassium salts are especially preferred.

Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, especially ethyl-, propyl-, diethyl- or triethylamine, but particulary isopropylamine and diethanolamine.

Examples of quaternary ammonium bases are in general the cations of hydroxyammonium salts, for example the tetramethylammonium cation, the trimethylbenzylammonium cation, the triethylbenzylammonium cation, the tetraethylammonium cation or the trimethylethylammonium cation, but also the ammonium cation.

The skilled artisan will appreciate that the introduction of certain substituents will create asymmetry in the compounds of Formula I. The present invention contemplates all enantiomers and mixtures of enantiomers, including racemates. It is preferred that the compounds of the invention containing chiral centers are single enantiomers. The present invention further contemplates all diastereomers.

The compounds of the present invention can be prepared by a variety of procedures, some of which are illustrated in the Schemes below. It will be recognized by one of skill in the art that the individual steps in the following schemes may be varied to provide the compounds of Formula I. Some of these variations are discussed.

The particular order of steps required to produce the compounds of Formula I is dependent upon the particular compound being synthesized, the starting compound, and the relative lability of the substituted moieties.

The compounds of the present invention may be prepared by methods well known to one of ordinary skill in the art. Generally, the compounds of Formula I are prepared by coupling an appropriately substituted bicyclylsulfonamide with an appropriately substituted benzoic acid as illustrated in the following schemes. The variables $R^1$, $R^2$, and Ar are as previously defined.

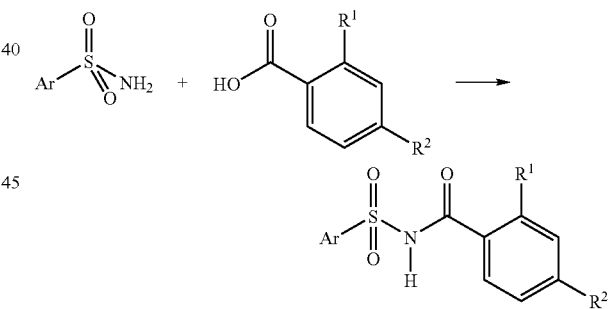

Synthetic Scheme I

The optionally substituted benzoic acid is coupled to an appropriate bicyclylsulfonamide under standard peptide coupling conditions well known to the skilled artisan. Specifically, the bicyclylsulfonamide and the benzoic acid are coupled in the presence of a peptide coupling reagent, optionally in the presence of a catalyst. Suitable peptide coupling reagents include N,N'-carbonyldiimidazole (CDI), N,N'-dicyclohexylcarbodiimide (DCC), 1-(3-dimethylaminopropyl)-3-ethylcarbodiimide hydrochloride (EDC), and 1-(3-(1-pyrrolidinyl)propyl)-3-ethylcarbodiimide (PEPC). Polymer supported forms of EDC (*Tetrahedron Letters*, 34(48), 7685 (1993)) and PEPC (U.S. Pat. No. 5,792,763) have been described, and are very useful for the preparation of the compounds of the present invention. Suitable catalysts for the coupling reaction include N,N-dimethyl-4-aminopyridine (DMAP). All of the reagents are combined in a suitable solvent, typically dichloromethane, chloroform, tetrahydrofuran, dioxane, or diethyl ether and are stirred for from 1 to 72 hours at a temperature of from ambient to about the reflux temperature of the solvent. The desired product may be isolated by standard extractive and crystallization techniques, and purified by chromatography or crystallization as necessary or desired. Where polymer-bound reagents are employed, they may be conveniently removed from the reaction mixture by filtration.

The requisite benzoic acids and sulfonamides are either commercially available or may be prepared by methods well known to the skilled artisan. See, for example, EP 583960.

The variables $R^1$ and $R^2$ are as previously defined and Z is a halide or cyano group.

Synthetic Scheme II

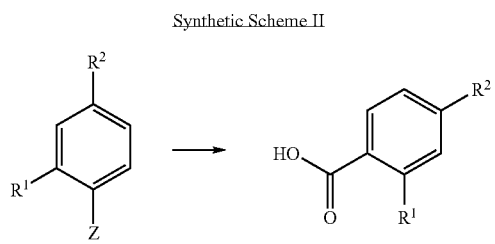

The preparation of the requisite benzoic acids may be accomplished by functional transformations well known to the skilled artisan as illustrated in Synthetic Scheme II. For example, when Z is a cyano group the conversion to the carboxylic acid can be achieved under acidic conditions (Larock, R. C., *Comprehensive Organic Transformations*, $2^{nd}$ *Ed.*, copyright 1999, John Wiley & Sons, pp 1986-1987). When Z is a halide a metal promoted carbonylation can be performed with palladium acetate and carbon monoxide in methanol to give the methyl benzoate (Id. at 1685-1687), then followed by a hydrolysis to afford the requisite benzoic acid (Id. at 1959-1968).

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example "° C.", "N", "mmol", "g", "mL", "M", "HPLC", "ES(- or +)MS", APC(+)MS and "$^1$H NMR", refer to degrees Celsius, normal or normality, millimole or millimoles, gram or grams, milliliter or milliliters, molar or molarity, high performance liquid chromatography, electron spray mass spectrometry, atmospheric pressure chemical ionization mass spectrometry, and proton nuclear magnetic resonance spectrometry, respectively.

Preparation 1

Benzo[1,3]dioxole-5-sulfonamide

Sulfuryl chloride (0.18 mol; 24.3 g) is added dropwise to cooled DMF (0.18 mol; 13.14 g) at a rate to maintain <10° C. The reaction complex is stirred at <10° C. for 30 min. 1,3-Benzodioxole is added dropwise over a period of 10 min. The reaction is then warmed to 80° C. and held for 10 min, and finally warmed to 110° C. and held for 10 min. During heating, the reaction turns brown and HCl evolution is observed. The reaction is cooled to room temperature and left overnight under nitrogen. Next, the reaction is poured onto ice (~150 g), chloroform (70 mL) and water (70 mL). The organic layer is collected and dripped into concentrated ammonium hydroxide (70 mL), yielding a precipitate, which is collected by filtration, washed with water and dried in vacuo at 40° C. to produce 10.28 g of benzo(1,3)dioxole-5-sulfonamide.

ES(−)MS m/z 200, (M−H)$^-$.

Preparation 2

2,4-Dibromobenzoic acid

A stirred suspension of 2,4-dibromobenzonitrile (1.57 g, 6.0 mmol) in sulfuric acid (6 M, 150 mL) is heated to reflux for 3 days. The reaction mixture is cooled to ambient temperature before being extracted with ethyl acetate (2×75 mL). The combined organic layers are washed with water (100 mL) and brine (50 mL), dried, concentrated, and then chromatographed on silica (acetic acid/methyl alcohol/chloroform, 0.1:0.5:99.4) to give the title compound (0.81 g, 48% yield). mp 171-172° C.;

ES(−)MS m/z 277, (M−H)$^-$ consistent with 2 Br.

Preparation 3

Benzo[b]thiophene-2-sulfonamide

To a stirred solution of benzo[b]thiophene (2.2 mmol) in dry THF (1.5 mL) is cooled to 0° C. and is slowly added 1.6 M n-BuLi in hexane (1.6 mL, 2.5 mmol). The temperature is maintained at 0° C. and the reaction mixture is stirred for 20 min. Then the heterogeneous mixture is diluted with 2 mL of THF and is transferred by canula to a well-stirred solution of sulfuryl chloride (368 µL, 4.6 mmol) in hexane (1.5 mL) at 0° C. After 1 hr, the suspension is diluted with acetone and the resulting solution of the corresponding sulfonyl chloride is added slowly to a solution of 2 mL of NH$_4$OH in acetone (5 mL). The mixture is diluted with water and acidified with concentrated HCl. The white precipitated sulfonamide is filtrated and dissolved in NaOH (0.5 N) and extracted with ethyl ether. The aqueous phase is acidified and the product is extracted into ethyl acetate. The organic phase is washed with water and brine, dried over Na$_2$SO$_4$ and concentrated in vacuo to afford the title compound (200 mg, 42%). ES(−)MS m/z 212, (M−H)$^-$.

Preparation 4

Benzo[b]thiophene-6-sulfonamide

To a solution of 6-bromothiophene (1.7 g, 8.1 mmol) in Et$_2$O (38 mL) at −78° C. is added a solution of t-BuLi (10.9 ml of 1.7 M in pentane, 18.6 mmol) dropwise. The reaction mixture is stirred at −78° C. for 1 hr then warmed to 0° C.

for 5 min then re-cooled to –78° C. Sulfur dioxide is bubbled over the solution for 5 min and the reaction is allowed to warm to room temperature overnight. N-Chlorosuccinimide (3.2 g, 24.3 mmol) is added and the reaction mixture is stirred for 2 hr. The organic layer is filtered under vacuum and the precipitate is washed with Et$_2$O. The filtrate is concentrated under vacuum to give the crude sulfonyl chloride. The crude sulfonyl chloride is dissolved in acetone (25 mL) and added to a solution of concentrated NH$_4$OH (10 mL) at 0° C. The reaction is stirred for 1 hr and partitioned between EtOAc and H$_2$O. The aqueous layer is separated and extracted with EtOAc (2×). The combined organic layers are dried (MgSO$_4$), filtered and evaporated to give the crude product. The crude product is triturated with hexanes/CH$_2$Cl$_2$ (2×) and i-PrOH/hexanes then dried under vacuum to afford the title compound (721 mg, 42%).

ES(–)MS m/z 212, (–H)$^-$.

Preparation 5

Thieno[3,2-b]pyridine-2-sulfonamide

A solution of n-BuLi (11 mL of 1.6 M in hexanes, 17.4 mmol) is added dropwise to a solution of thieno[3,2-b]pyridine (1.17 g, 8.7 mmol) in anhydrous THF (10 mL) under nitrogen at –70° C. The mixture is warmed to 0° C. and stirred for 10 min. The reaction mixture is diluted with THF (10 mL). The suspension is transferred by canula to a well-stirred solution of sulfuryl chloride (2.8 mL, 34.8 mmol) in hexanes (10 mL) at 0° C. The mixture is stirred for 1 hr. After 1 hr, the yellow suspension is concentrated under vacuum. The residue is dissolved in acetone (20 mL) and added slowly to a solution of 29% NH$_4$OH (10 mL) in acetone (30 mL). The mixture is stirred for 2 hr. The organic solvents are removed under vacuum and the residue is extracted with EtOAc (400 mL). The organic layer is washed with brine then dried (Na$_2$SO$_4$), filtered and evaporated under reduced pressure. The crude product is chromatographed on silica gel, eluting with CH$_2$Cl$_2$:MeOH (30:1) to afford the title compound(450 mg, 24%).

APC(+)MS m/z 215, (M+H)$^+$.

Preparation 6

Benzofuran-6-sulfonamide

To a stirred solution of 6-bromobenzofuran (1.73 g, 8.78 mmol) in Et$_2$O (41 mL) at –78° C. is added t-BuLi (12 ml of 1.7 M in pentane, 20.18 mmol) dropwise. The reaction mixture is stirred at –78° C. for 1 hr then warmed to 0° C. for 5 min then re-cooled to –78° C. Sulfur dioxide is bubbled over the solution for 5 min and the reaction is allowed to warm to room temperature overnight. N-Chlorosuccinimide (3.5 g, 26.34 mmol) is added and the reaction is stirred for 1.5 hr then filtered and the precipitate washed with Et$_2$O. The filtrate is concentrated under vacuum to give the crude sulfonyl chloride, which dissolves in acetone (25 mL), and is cooled to 0° C. A solution of concentrated NH$_4$OH (10 ml) is then added. The reaction mixture is stirred for 1 hr then partitioned between EtOAc and H$_2$O. The aqueous layer is separated and extracted with EtOAc (2×). The combined organic layers are dried (MgSO$_4$), filtered and evaporated under vacuum to give the crude product. The crude product was triturated with hexanes/CH$_2$Cl$_2$ (9:1) and the solids dried under vacuum to afford the title compound (540 mg, 31%) as a brown solid.

ES(–)MS m/z 196, (M–H)$^-$.

Preparation 7

Benzo[b]thiophene-5-sulfonamide

To a suspension of 5-bromobenzo[b]thiophene (2.13 g, 10 mmol) in Et$_2$O (50 mL) at –70° C. is added slowly a solution of t-BuLi (12 mL of 1.7 M in pentane, 20 mmol). The reaction mixture is stirred at below –70° C. for 1 hr and then warmed to 0° C. Sulfur dioxide is bubbled into the solution for 5 min. The reaction is warmed to room temperature and stirred for 15 hr. N-Chlorosuccinimide (1.34 g, 10 mmol) is added to the resulting suspension and the mixture is stirred at room temperature for 3 hr. The reaction mixture is filtered and the solids are washed with Et$_2$O. The filtrate is concentrated in vacuo. The residue is dissolved in acetone (30 mL) and added to a solution of 29% NH$_4$OH (20 mL) in acetone (50 mL) at 0° C. The reaction mixture is stirred at 0° C. for 0.5 hr. The organic solvent is removed under reduced pressure and the residue extracted with EtOAc (2×250 mL). The combined organic extracts are washed with brine then dried (Na$_2$SO$_4$), filtered and concentrated in vacuo. The crude product is chromatographed on silica gel, eluting with CH$_2$Cl$_2$ to afford the title compound (910 mg, 43%).

ES(+)MS m/z 214, (M+H)$^+$.

Preparation 8

Benzofuran-2-sulfonamide

To a stirred solution of benzo[b]furane (2.5 mmol) in dry THF (1.5 mL) and cooled to 0° C. is slowly added 1.6 M n-BuLi in hexane (1.7 mL, 2.5 mmol). The temperature is maintained at 0° C. and the reaction mixture is stirred for 20 min. Then the heterogeneous mixture is diluted with 2 mL of THF and is transferred by canula to a well-stirred solution of sulfuryl chloride (410 µL, 5.1 mmol) in hexane (2.0 mL) at 0° C. After 1 hr, the suspension is diluted with acetone and the resulting solution of the corresponding sulfonyl chloride is added slowly to a solution of 2 mL of NH$_4$OH in acetone (5 mL). The mixture is diluted with water and acidified with concentrated HCl and the product extracted into ethyl acetate. The organic phase is washed with water and brine, dried over Na$_2$SO$_4$ and concentrated in vacuo. The crude product is purified by silica gel chromatography (eluent: hexane 4/ethyl acetate 1) to afford the title compound (211 mg, 43%).

ES(–)MS m/z 196 (M–H)$^-$.

Preparation 9

Benzothiazole-6-sulfonamide

2-Amino-benzothiazole-6-sulfonamide is prepared according to literature in two steps from sulfanilamide. (Getman, D. P.; De Crescenzo, G. A.; Freskos, J. N.; Vazquez, M. L.; Sikorski, J. A.; Deyadas, B.; Nagarajan, S.; Brown, D. L.; McDonald, J. J. U.S. Pat. No. 6,172,101 (B), 2001.). 2-Amino-6-sulfonamidobenzothiazole (2.00 mmol) is dissolved in a mixture of 1,4-dioxane (4 mL) and DMF (1 mL) and treated with isoamylnitrite (335 µL, 2.5 mmol). The reaction mixture is heated to 85° C. for 2 hr, then cooled and concentrated by rotary evaporation to remove the dioxane. The crude deaminated benzothiazole-6-sulfonamide is used without purification.

Preparation 10

5-Methyl-benzo[b]thiophene-2-sulfonamide

5-Methyl-benzo[b]thiophene (220 mg, 1.5 mmol) is dissolved in dry THF (1.5 mL) and cooled to 0° C. To this solution is slowly added 1.6 M n-BuLi in hexane (1.0 mL, 1.6 mmol) and the temperature maintained at 0° C. and the reaction mixture stirred for 20 min. Then the heterogeneous mixture is diluted with 2 mL of THF and transferred by canula to a well-stirred solution of sulfuryl chloride (245 µL, 4.6 mmol) in hexane (1.5 mL) at 0° C. After 1 hr, the suspension is diluted with acetone and the resulting solution of acid chloride is added slowly to a solution of 2 mL of $NH_4OH$ in acetone (5 mL). The mixture is diluted with water and acidified with conc. HCl. The aqueous solution is acidified and the product is extracted into ethyl acetate. The organic phase is washed with water and brine, dried ($Na_2SO_4$), and evaporated. The crude product is purified by silica gel chromatography (eluent: hexane 3/ethyl acetate 1) to afford the title compound (53 mg, 16%).

Preparation 11

6-Methylbenzo[b]thiophene-2-sulfonamide

Prepared similarly to PREPARATION 10.

Preparation 12

Indane-5-sulfonamide

To a solution of indane (50 mmol, 6.11 mL) in dichloromethane (50 mL) at 0° C. is added dropwise chlorosulfonic acid (200 mmol, 13.3 mL). The resulting solution is allowed to return to room temperature and stirred for 2 hrs. The solution is then poured slowly onto a mixture of ice (200 g) and dichloromethane (50 mL). The organic layer is separated, washed with brine (50 mL), dried over sodium sulfate, filtered and evaporated to produce indan-5-sulfonic acid chloride.

To the crude sulfonyl chloride is added concentrated ammonium hydroxide (60 mL). The mixture is warmed to 60° C., cooled to room temperature and diluted with water (60 mL). Indan-5-sulfonic acid amide is collected by filtration, washed with water and dried in vacuo at 60 deg.

Preparations 13 and 14

1-Oxo-indan-5-sulfonamide and
3-oxo-indan-5-sulfonamide

To a solution of indane (50 mmol, 6.11 mL) in dichloromethane (50 ml) at 0° C. is added dropwise chlorosulfonic acid (200 mmol, 13.3 ml). The resulting solution is allowed to return to room temperature and is stirred for 2 hr. The solution is then poured slowly onto a mixture of ice (200 g) and dichloromethane (50 ml). The organic layer is separated, washed with brine (50 mL), dried over sodium sulfate, filtered and evaporated to produce indan-5-sulfonic acid chloride.

To the crude sulfonyl chloride is added concentrated ammonium hydroxide (60 mL). The mixture is warmed to 60° C., cooled to room temperature and diluted with water (60 mL). Indan-5-sulfonamide is collected by filtration, washed with water and dried in vacuo at 60° C.

A solution of the crude sulfonamide (25 mmol) in acetone (60 mL) is cooled to 5-10° C. during dropwise addition of 2.86M Jones reagent (200 mmol, 70 mL). The resulting mixture is stirred at 5-10° C. for 4 hr. Excess Jones reagent is destroyed with i-propanol, and the resulting green gummy mass is filtered through celite, then washed sequentially with THF and acetone. The filtrate is evaporated and the residue is dissolved in THF, washed with saturated sodium bicarbonate solution, dried over sodium sulfate and evaporated. The crude product (2.0 g) is purified by separation on a fluorisil column, eluting with a gradient from 10% hexane: ethyl acetate to 50% hexane:ethyl acetate. Two products are collected: 1-oxo-indan-5-sulfonamide and 3-oxo-indan-5-sulfonamide.

1-oxo-indan-5-sulfonamide: $^1$H NMR (300 MHz, DMSO-d6) δ: 8.02-8.09 (m, 2H, J=8.05 Hz, 1.83 Hz), 7.78 (d, 1H, J=8.05), 7.48 (s, 2H, NH2), 3.18 (t, 2H, J=5.86), 2.72 (t, 2H, J=5.86).

3-oxo-indan-5-sulfonamide: $^1$H NMR (300 MHz, DMSO-d6) δ: 8.01 (s, 1H), 7.77-7.86 (m, 2H, J=), 7.56 (s, 2H, NH2), 3.18 (t, 2H, J=5.86), 2.71(t, 2H, J=5.86).

Preparation 15

1-Methyl-1H-indole-2-sulfonamide

1-Methyl-1H-indole (3.07 mL; 24.0 mmol) is dissolved in anhydrous, stabilized tetrahydrofuran (100 mL). The solution is cooled to 0° C., mixed with 1.7 M n-BuLi in hexanes (42 mL; 72 mmol; 3 equiv), and stirred for 1.2 hr. After cooling the resulting suspension to −40° C., sulfur dioxide gas is bubbled into the reaction mixture for 0.25 hr. The cloudy orange solution is stirred at −40° C. for 1 hr and 0° C. for the next hour. A precipitation with hexanes (125 mL), followed by filtration, re-suspension of the filtrate in dichloromethane (200 mL), and cooling of the solution to −20° C., precedes addition of N-chlorosuccinimide (3.52 g; 26.4 mmol; 1.1 equiv). After stirring the reaction mixture overnight, anhydrous ammonia gas is bubbled into the reaction for 0.25 hr. Following concentration in vacuo, the resulting solids are partitioned between 1N HCl(aq) and dichloromethane. The aqueous layer is washed twice with dichloromethane and twice with ethyl acetate. The combined organic layers are dried with $Na_2SO_4$(s), filtered, and concentrated in vacuo. Isolation of the product by silica chromatography with a step gradient of methanol in dichloromethane produces a brown oil (1.4 g; 28% yield) that is used without further purification.

ES(−)MS m/z 209, (M−H)$^-$.

General Coupling Procedure

To a stirring solution of the benzoic acid (1.25 eq) in dry dichloromethane (10 mL/mmol), the phenylsulfonamide (1.0 eq) is added in one portion followed by EDC (1.2-1.5 eq) and finally, N,N-[dimethyl]-4-aminopyridine (1.2 equiv). The mixture is vigorously stirred under nitrogen for 16 hr, concentrated under reduced pressure, and the residue partitioned between ethyl acetate and water. The organic layer is washed with 1 N hydrochloric acid (4×20 mL/mmol). The combined organic layers are finally washed with water and saturated aqueous sodium chloride, dried over sodium sulfate and concentrated under reduced pressure. The residue can be subjected to silica gel chromatography or crystallization if necessary or desired.

The compounds of EXAMPLES 1-31 are prepared essentially as described in this general coupling procedure.

| EXAMPLE # | Product | Mass Spectral Data (m/z) |
|---|---|---|
| 1 | N-[4-chloro-2-methylbenzoyl]-2,3-dihydrobenzofuran-5-sulfonamide | ES(−)MS m/z 350, (M − H)⁻ consistent with 1 Cl. |
| 2 | N-[4-chloro-2-bromobenzoyl]-benzo[1,3]dioxole-5-sulfonamide | ES(−)MS m/z 416, (M − H)⁻ consistent with 1 Br and 1 Cl. |
| 3 | N-[4-chloro-2-methylbenzoyl]-benzo[1,3]dioxole-5-sulfonamide | ES(−)MS m/z 352, (M − H)⁻ consistent with 1 Cl. |
| 4 | N-[4-bromo-2-methylbenzoyl]-benzo[1,3]dioxole-5-sulfonamide | ES(−)MS m/z 396, (M − H)⁻ consistent with 1 Br. |
| 5 | N-[4-methyl-2-bromobenzoyl]-benzo[1,3]dioxole-5-sulfonamide | ES(−)MS m/z 396, (M − H)⁻ consistent with 1 Br. |
| 6 | N-[2,4-dibromobenzoyl]-benzo[1,3]dioxole-5-sulfonamide | ES(+)MS, m/z 462, (M + H)⁺ consistent with 2 Br. |
| 7 | N-[4-bromo-2-chlorobenzoyl]-benzo[1,3]dioxole-5-sulfonamide | ES(−)MS m/z 416, (M − H)⁻ consistent with 1 Br and 1 Cl. |
| 8 | N-[2,4-dichlorobenzoyl]-dibenzofuran-2-sulfonamide | ES(+)MS m/z 420, (M + H)⁺ consistent with 2 Cl. |
| 9 | N-[2,4-dichlorobenzoyl]-benzocyclobutane-1-sulfonamide | ES(+)MS m/z 356, (M + H)⁺ consistent with Cl. |
| 10 | N-[2,4-dichlorobenzoyl]-benzo[b]thiophene-6-sulfonamide | ES(−)MS m/z 384, (M − H)⁻ consistent with 2 Cl. |
| 11 | N-[4-bromo-2-methylbenzoyl]-thieno[3,2-b]pyridine-2-sulfonamide | ES(+)MS m/z 411, (M + H)⁺ consistent with 1 Br. |
| 12 | N-[2,4-dichloro-benzoyl]-thieno[3,2-b]pyridine-2-sulfonamide | ES(+)MS m/z 387, (M + H)⁺ consistent with 2 Cl. |
| 13 | N-[4-bromo-2-methylbenzoyl]-benzofuran-6-sulfonamide | ES(+)MS m/z 394, (M + H)⁺ consistent with 1 Br. |
| 14 | N-[4-bromo-2-methylbenzoyl]-benzo[b]thiophene-5-sulfonamide | ES(−)MS m/z 408, (M − H)⁻ consistent with 1 Br. |
| 15 | N-[2,4-dichlorobenzoyl]-benzo[b]thiophene-5-sulfonamide | ES(+)MS m/z 386, (M + H)⁺ consistent with 2 Cl. |
| 16 | N-[2,4-dichlorobenzoyl]-benzo[b]thiophene-2-sulfonamide | ES(−)MS m/z 384, (M − H)⁻ consistent with 2 Cl. |
| 17 | N-[2,4-dichlorobenzoyl]-benzofuran-2-sulfonamide | ES(−)MS m/z 368, (M − H)⁻ consistent with 2 Cl. |
| 18 | N-[2,4-dichlorobenzoyl]-benzothiazole-6-sulfonamide | ES(+)MS m/z 387, (M + H)⁺ consistent with 2 Cl. |
| 19 | N-[2-methyl-4-chlorobenzoyl]-benzothiazole-6-sulfonamide | ES(+)MS m/z 367, (M + H)⁺ consistent with 2 Cl. |
| 20 | N-[2-methyl-4-bromobenzoyl]-benzothiazole-6-sulfonamide | ES(+)MS m/z 411, (M + H)⁺ consistent with 1 Br. |
| 21 | N-[2,4-dichlorobenzoyl]-5-methylbenzo[b]thiophene-2-sulfonamide. | ES(−)MS m/z 398, (M − H)⁻ consistent with 2 Cl. |
| 22 | N-[2,4-dichlorobenzoyl]-6-methylbenzo[b]thiophene-2-sulfonamide | ES(−)MS m/z 398, (M − H)⁻ consistent with 2 Cl. |
| 23 | N-[2,4-dichlorobenzoyl]-2,3-dihydrobenzo[1,4]dioxane-6-sulfonamide | ES(−)MS m/z 386, (M − H)⁻ consistent with 2 Cl. |
| 24 | N-[2,4-dichlorobenzoyl]-tetrahydrobenzofuran-5-sulfonamide | ES(−)MS m/z 370, (M − H)⁻ consistent with 2 Cl. |

-continued

The compounds of EXAMPLES 1-31 are prepared essentially as described in this general coupling procedure.

| EXAMPLE # | Product | Mass Spectral Data (m/z) |
|---|---|---|
| 25 | N-[2,4-dichlorobenzoyl]-benzo[1,3]dioxole-5-sulfonamide | ES(−)MS m/z 372, (M − H)− consistent with 2 Cl. |
| 26 | N-[2,4-dichlorobenzoyl]-1-methyl-2,3-dihydro-1H-indole-6-sulfonamide | ES(−)MS m/z 383, (M − H)− consistent with Cl. |
| 27 | N-[2,4-dichlorobenzoyl]-3H-indene-5-sulfonamide | ES(−)MS m/z 366, (M − H)− consistent with 2 Cl. |
| 28 | N-[2,4-dichlorobenzoyl]-indane-5-sulfonamide | ES(−)MS m/z 368, (M − H)− consistent with 2 Cl. |
| 29 | N-[2,4-dichlorobenzoyl]-1-oxo-indane-5-sulfonamide | ES(−)MS m/z 382, (M − H)− consistent with 2 Cl. |
| 30 | N-[2,4-dichlorobenzoyl]-3-oxo-indane-5-sulfonamide | ES(−)MS m/z 382, (M − H)− consistent with 2 Cl. |
| 31 | N-[2,4-dichlorobenzoyl]-1-methyl-indole-2-sulfonamide | ES(−)MS m/z 381 (M − H)− consistent with 2 Cl. |

EXAMPLE 32

N-[2,4-dichlorobenzoyl]-naphthalene-2-sulfonamide

An 8 mL reaction vial is charged with 0.39 mmol (1.5 eq) of 2,4 dichlorobenzoic acid. 2.0 mL of $CH_2Cl_2$ is then added to the acid.

A stock solution of naphthalene-2-sulfonamide and DMAP in $CH_2Cl_2$ is made so that 0.26 mmol (1 eq) of the sulfonamide and 48 mg (0.39 mmol, 1.5 eq) of DMAP can be delivered to each reaction vial in 4.0 mL of stock solution.

The 4.0 mL of stock solution is then added to the reaction vials containing the benzoic acid. The vials are capped and shook. At least 0.261 g (loading=2.0 mmol/g, 0.52 mmol, 2.0 eq) of carbodiimide polystyrene resin is added to the reaction vials. The vials are rotated over the weekend. Thin layer chromatography is then conducted with 10% MeOH: $CH_2Cl_2$ as the eluant to access reaction mixtures.

At least 0.77 g (4.5 eq, loading=1.53 mmol/g, 1.17 mmol)of MP-TsOH (sulphonated polystyrene resin that is the resin-bound equivalent to p-toluenesulfonic acid) is added to each reaction vial. The vials are rotated overnight. The resins are then filtered off and the reaction mixtures collected. The reaction mixtures are purified using reverse phase HPLC.

ES(−)MS m/z 378, (M−H)− consistent with 2 Cl.

EXAMPLE 33

N-[2,4-dichlorobenzoyl]-benzofuran-6-sulfonamide

To a solution of benzofuran-6-sulfonamide (120 mg, 0.608 mmol) in $CH_2Cl_2$ (3.6 mL) and pyridine (2.3 mL) is added DMAP (75 mg, 0.611 mmol) and 2,4-dichlorobenzoyl chloride (153 mg, 0.730 mmol) and the reaction is stirred at room temperature overnight. The reaction mixture is diluted with $CH_2Cl_2$ then washed with 2 M HCl (2×) and dried ($MgSO_4$). The organic solution is filtered and evaporated under vacuum to give the crude product. Flash chromatography on silica gel eluting with a gradient {$CH_2Cl_2$ to $CH_2Cl_2$:(CHCl$_3$:MeOH) [4:1(9:1)]} gives the title compound as a tan solid. ES(−)MS m/z 368, (M−H)− consistent with 2 Cl.

All of the compounds concerned are orally available and are normally administered orally, and so oral administration is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent for capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate; disintegrating agents such as: croscarmellose, crospovidone, sodium starch glycolate, corn starch and the like; lubricants such as: magnesium stearate, steric acid, talc or hydrogenated vegetable oil; glidants such as colloidal silicon dioxide; wetting agents such as: sodium lauryl sulfate and polysorbate 80 (CAS No. 9005-65-6); and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

Injections for parenteral administration include sterile aqueous or non-aqueous solutions, suspensions and emulsions. Aqueous solutions and suspensions may include distilled water for injection or physiological salt solution. Non-aqueous solutions and suspensions may include propylene glycol, polyethylene glycol, vegetable oil such as olive oil, alcohol such as ethanol or polysorbate 80. Injections may comprise additional ingredients other than inert diluents: e.g. preserving agents, wetting agents, emulsifying agents, dispersing agents, stabilizing agents (such as lactose), assisting agents such as agents to assist dissolution (e.g. glutamic acid or aspartic acid). They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile diluent(s) for injection immediately before use.

The compounds of Formula I are generally effective over a wide dosage range. For example, dosages per day normally fall within the range of about 10 to about 300 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

Inhibition of HUVEC Proliferation

Human umbilical vein endothelial cells (HUVEC; Bio Whittaker/Clonetics, Walkersville, Md.) were maintained in endothelial cell growth medium (EGM) containing basal medium (EBM) with bovine brain extract, human epidermal growth factor, hydrocortisone, gentamicin, amphotericin B and 2% fetal bovine serum. For the assay, HUVEC ($5 \times 10^3$) in EBM (200 µl) with 0.5% fetal bovine serum were added to wells in a 96-well cell culture plate and incubated at 37° C. for 24 hr in humidified 5% carbon dioxide/air. The test compounds were serially diluted in dimethyl sulfoxide (DMSO) in concentrations from 0.0013 to 40 µM and added to the wells in 20 µl. Then human vascular endothelial growth factor (VEGF) (20 ng/mL in wells; R&D Systems, Minneapolis, Minn.) prepared from a stock solution of 100 µg/mL in phosphate buffered normal saline containing 0.1% bovine serum albumin, was added to the wells. The HUVEC were incubated at 37° C. for 72 hr in humidified 5% carbon dioxide/air. WST-1 cell proliferation reagent (20 µl; Boehringer Mannheim, Indianapolis, Ind.) was added to the wells and the plates returned to the incubator for 1 hr. The absorbance of each well at 440 nm was measured. The growth fraction was determined from the absorbance of treated wells with and without VEGF divided by the absorbance obtained from control wells set to zero and 1.0. The exemplified compounds were tested in this assay and all exhibited an $IC_{50} \leq 1.2$ µM.

HCT116 Colon Carcinoma Cell Growth Inhibition

Human HCT116 colon carcinoma cells were grown monolayer culture in RPMI 1640 medium supplemented with 10% fetal bovine serum and 1% penicillin-streptomycin (GibcoBRL, Grand Island, N.Y.). HCT116 cells in exponential growth phase were exposed to various concentrations of the test compounds at 37° C. for 72 hr in 5% carbon dioxide/air. After exposure to the agent, the cells were washed with 0.9% phosphate buffered saline. Growth inhibition was determined using WST-1 cell proliferation reagent as described above. The results are expressed as the growth fraction of treated cells compared with control cultures. Representative compounds of the present invention were tested for efficacy against the human colon HCT116 tumor cells. The data from these experiments are summarized in TABLE I.

TABLE I

| EXAMPLE | $IC_{50}$ (µM) |
| --- | --- |
| 1 | 9.6 |
| 2 | 3.9 |
| 3 | 6.4 |
| 4 | 7.5 |
| 5 | 8.5 |
| 6 | 4.6 |
| 7 | 13.9 |
| 16 | 21.8 |
| 17 | 19.8 |
| 18 | 14.2 |
| 23 | 4.1 |
| 24 | 40.0 |
| 25 | 2.1 |
| 26 | 10.0 |
| 27 | 3.2 |
| 28 | 3.2 |
| 29 | 26.2 |
| 31 | 4.6 |

We claim:

1. A compound of Formula I:

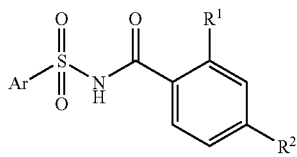

where:

Ar is a heterocycle selected from the group consisting of benzothien-2-yl, benzothien-5-yl, and benzothien-6-yl;

$R^1$ and $R^2$ are either both halo, both trifluoromethyl, or one is halo and the other is $C_1$-$C_6$ alkyl; or a pharmaceutically acceptable base addition salt thereof.

2. The compound of claim 1, wherein the compound is a pharmaceutically acceptable base addition salt.

3. The compound of claim 2, wherein the pharmaceutically acceptable base addition salt is a sodium salt.

4. A method of treating susceptible neoplasms, wherein the susceptible neoplasm is adenocarcinoma of the colon and rectum, in a mammal comprising administering to a mammal in need of such treatment an oncolytically effective amount of a compound of Formula I:

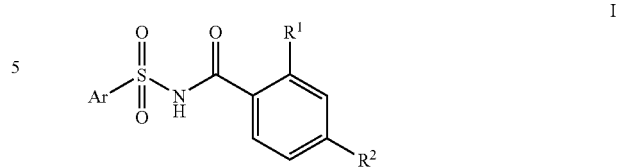

where:

Ar is a heterocycle selected from the group consisting of benzothien-2-yl, benzothien-5-yl and benzothien-6-yl;

$R^1$ and $R^2$ are either both halo, both trifluoromethyl, or one is halo and the other is $C_1$-$C_6$ alkyl; or a pharmaceutically acceptable base addition salt thereof.

5. A pharmaceutical formulation comprising a compound of Formula I:

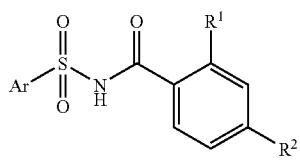

where:

Ar is a heterocycle selected from the group consisting;

$R^1$ and $R^2$ are either both halo, both trifluoromethyl, or one is halo and the other is $C_1$-$C_6$ alkyl; or a pharmaceutically acceptable base addition salt thereof and a pharmaceutically acceptable carrier, diluent, or excipient.

* * * * *

UNITED STATES PATENT AND TRADEMARK OFFICE
CERTIFICATE OF CORRECTION

PATENT NO. : 7,282,595 B2
APPLICATION NO. : 10/535002
DATED : October 16, 2007
INVENTOR(S) : Mary Margaret Mader et al.

It is certified that error appears in the above-identified patent and that said Letters Patent is hereby corrected as shown below:

On the Title page, directly below Item (65), please add the following:

"Related U.S. Application Data
(60) Provisional Application No. 60/428,891 filed on November 22, 2002".

Signed and Sealed this
Twenty-sixth Day of February, 2013

Teresa Stanek Rea
*Acting Director of the United States Patent and Trademark Office*